United States Patent [19]

Fokas et al.

[11] Patent Number: 6,114,540
[45] Date of Patent: Sep. 5, 2000

[54] SPIRO[PYRROLIDINE-2,3'-OXINDOLE] COMPOUNDS AND METHODS OF USE

[75] Inventors: Demosthenes Fokas, Somerville; David L. Coffen, Cambridge; William J. Ryan, Woburn, all of Mass.

[73] Assignee: ArQule, Inc., Woburn, Mass.

[21] Appl. No.: 09/149,147

[22] Filed: Sep. 8, 1998

Related U.S. Application Data

[60] Provisional application No. 60/058,450, Sep. 8, 1997.

[51] Int. Cl.[7] ............... C07D 209/96; C07D 487/10; C07D 513/10
[52] U.S. Cl. ............... 548/410; 548/411; 548/147; 548/159; 548/179
[58] Field of Search ............... 548/147, 410, 548/411

[56] References Cited

U.S. PATENT DOCUMENTS 5,958,792  9/1999  Desai et al. ............... 436/518

OTHER PUBLICATIONS

Casaschi et al., "Retention of the Configuration of Oxoindolin–3–Ylidene Dipolarophiles in the Reaction with Azomethine Ylides from Ninhydrin and Secondary Amino Acids", *Gazzetta Chimica Italiana*, 123, pp. 137–143, 1993.

Grigg et al., "Decarboxylative Transamination. A New Route to Spirocyclic and Bridgehead–nitrogen Compounds. Relevance to α–Amino Acid Decarboxylases", *J. Chem. Soc. Commun.*, 3, pp. 182–183, 1984.

Grigg et al., "Decarboxylative Transamination. Mechanism and Applications to the Synthesis of Heterocyclic Compounds", *J. Chem. Soc. Chem. Commun.*, 3, pp. 180–183, 1984.

Beckwith et al., "Tandem Radical Translocation and Homolytic Aromatic Substitution: a Convenient and Efficient Route to Oxindoles", *J. Chem. Soc. Chem. Commun.*, pp. 977–978, 1995.

Kornet et al., "Oxindole–3–spiropyrrolidines and –piperidines. Synthesis and Local Anesthetic Activity", *Journal of Medicinal Chemistry*, vol. 19, No. 7, pp. 892–898, 1976.

Ardill et al., "Iminium Ion Route to Azomethine Ylides from Primary and Secondary Amines", *J. Chem. Soc., Chem. Commun.*, pp. 602–604, 1986.

Ardill et al., "X=Y–ZH Compounds as Potential 1,3–Dipoles. Part 28.[1,2] The Iminium Ion Route to Azomethine Ylides. Background and Reaction of Amines with Bifunctional Ketones.", *Tetrahedron*, 46:18, pp. 6433–6448, 1990.

Coulter et al., "Chiral Induction in Cycloaddition Reactions of Azomethine Ylides Derived from Secondary α–Amino Acids by the Decarboxylative Route", *Tetrahedron Letters*, 32:39, pp. 5417–5420, 1991.

Jones et al., "Aryl Radical Cyclisation on to a Pyrrole Nucleus", *Tetrahedron Letters*, 36:37, pp. 6743–6744, 1995.

Asfah et al., "A study on the condensation of α, δ–diketoesters with Schiff bases", *Chemical Abstracts*, vol. 24, No. 19, Abstract No. 260756b, p. 1242, col. 1, 1996.

Marx et al., "Synthetic Design for Combinatorial Chemistry. Solution and Polymer–Supported Synthesis of Polycyclic Lactams by Intramolecular Cyclization of Azomethine Ylides", *J. Am. Chem. Soc.*, 119, pp. 6153–6167, 1997.

Fokas et al., "Solution Phase Synthesis of a Spiro[pyrrolidine–2,3'–oxindole] Library via a Three Component 1,3–Dipolar Cycloaddition Reaction", *Tetrahedron Letters*, 39, pp. 2235–2238, 1998.

Powers et al., "Automated Parallel Synthesis of Chalcone–Based Screening Libraries", *Tetrahedron*, 54 pp. 4085–4096, 1998.

*Primary Examiner*—Johann Richter
*Assistant Examiner*—Jane C. Oswecki
*Attorney, Agent, or Firm*—Fish & Richardson P.C.

[57] ABSTRACT

The invention provides spiro[pyrrolidine-2,3'-oxindole] compounds produced by the stereo- and regio-selective reaction of variously substituted isatins, α-amino acids, and dipolarophiles (e.g., trans-chalcones, acrylate esters, or vinyl oxindoles).

24 Claims, 6 Drawing Sheets

SPIRO[PYRROLIDINE-2,3'-OXINDOLE] COMPOUNDS AND METHODS OF USE

This application claims the benefit of Provisional Application No. 60/058,450 filed Sep. 8, 1997.

BACKGROUND OF THE INVENTION

The invention relates generally to spiro-[pyrrolidine-2,3'-oxindole] compounds, to combinatorial libraries of spiro [pyrrolidine-2,3'-oxindole] compounds, and to methods of synthesizing and assaying such libraries. The compounds can be formed, for example, via 1,3-dipolar cycloaddition of reactive isatin-amino acid adducts to substituted trans-chalcones and other dipolarophiles.

Oxindole alkaloids are a rich class of bioactive compounds. For example, gelsemine is a spirooxindole alkaloid that possesses central nervous system (CNS) stimulating activity. Other spirooxindoles are aldose reductase inhibitors and are used as antidiabetic drugs.

In classical drug design, many individual compounds are synthesized one at a time and then screened. This is a relatively labor-intensive process. An alternative approach is rational drug design. One aspect of rational drug design includes structure-guided methods. One structure-guided approach to the discovery of new pharmaceutically active organic drugs (e.g., compounds with the three-dimensional structure needed for binding) relies primarily on X-ray crystallography of purified receptors. Once a binding site is identified, organic molecules are designed to fit the available steric space and charge distribution. However, it is often difficult to obtain purified receptors, and still more difficult to crystallize the receptor so that X-ray crystallography can be applied.

Other methods such as homology modelling or nuclear magnetic resonance studies can also be used to identify the binding site, although it is still difficult to devise an appropriate ligand, even after the binding site has been properly identified. Overall, it is quite difficult to design useful pharmaceutically active compounds because of factors such as the difficulty in identifying receptors, purifying and identifying the structures of compounds which bind to those receptors, and thereafter synthesizing those compounds.

Another approach to the discovery of new drugs is through pharmacophore-guided design. If a number of molecules (e.g., biologically active compounds) are known to bind, for example, to a macromolecule, new compounds can be synthesized that mimic the known molecules. However, since the active moiety or active structural component of the active compound is usually unknown, the process of synthesizing new compounds relies primarily on trial and error and the synthesis and screening of each compound individually. This method is time consuming and expensive since the likelihood of success for any single compound is relatively low.

Rather than trying to determine the particular three-dimensional structure of a protein using crystallography or attempting to synthesize specific compounds that mimic a known biologically active compound, researchers have also developed assays to screen combinatorial libraries of candidate compounds. More specifically, those attempting to create biologically active compounds produce extremely large numbers of different compounds at the same time either within the same reaction vessel or in separate vessels. The synthesized combinatorial library is then assayed and active molecules are isolated (e.g., in the case of mixtures of compounds) and analyzed.

SUMMARY OF THE INVENTION

In general, the invention is based on the discovery that under the right conditions, variously substituted isatins, α-amino acids, and dipolarophiles (e.g., trans-chalcones, acrylate esters, or vinyl oxindoles) can stereo- and regio-selectively react to form libraries of spiro[pyrrolidine-2,3,'-oxindole] compounds. The new libraries can be assayed using any of many known screening procedures for activity, e.g., biological activity. For example, the libraries can be screened for activity as drugs (e.g., anticancer drugs, antibiotics, antiviral drugs, antiinflammatory drugs, analgesics, kinase inhibitors, immunomodulators, neuroleptics, sedatives, stimulants, or diagnostic aids), bioseparation agents (e.g., affinity ligands), or pesticides (e.g., herbicides, insecticides, or rodenticides).

In one embodiment, the invention features a method of synthesizing a library of compounds (e.g., including 10, 100, 5,000, 10,000, 100,000 or more compounds). The method includes reacting a plurality of isatins with a plurality of α-amino acids, independently, to form azomethine ylide compounds; and reacting the azomethine ylides with a plurality of dipolarophiles (e.g., chalcones, acrylate esters, vinyl oxindoles, fumarates, maleates, maleimides, cinnamonitriles, nitroolefins, acrylonitriles, vinyl sulfones, or vinyl sulfoxides), independently, to form the library of compounds.

The chalcones can be prepared, for example, by reacting each of a plurality of arylaldehydes, independently, with each of a plurality of acetophenone compounds. Certain acrylate esters (e.g., cinnamates) can be prepared, for example, by reacting each of a plurality of arylaldehydes with trimethylphosphonoacetate under Horner-Emmons condensation reaction conditions. Vinyloxindoles can be prepared, for example, by reacting oxindoles with arylaldehydes, or by reacting isatins with acetophenone compounds. Azomethine ylides can be prepared in situ in the presence of the dipolarophiles.

In certain cases, the library of compounds is prepared in a single compound-per-well format, wherein each well (e.g., a well of a 96-well plate, a test tube, a centrifuge tube, a flask, a beaker, or other container) contains predominantly a single member of a library of the invention.

In another embodiment, the invention features a chemical library that includes ten or more different compounds, each compound being produced from a reaction of each of a plurality of isatins with each of a plurality of α-amino acids, and with each of a plurality of dipolarophiles (e.g., in a [2+3] reaction as shown in FIG. 2). Each of the ten or more compounds is present in the library in a retrievable and analyzable amount.

The invention also features a chemical library that includes ten or more different compounds each present in a retrievable and analyzable amount. Each compound can be represented by the structural formula:

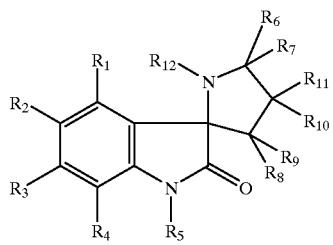

where $R_1$ to $R_4$, independently, can be hydrogen, alkyl, aryl, carbocyclic, fluoro, chloro, bromo, iodo, thio, hydroxyl, alkylthio, alkoxy, carboxy, sulfonyl, nitro, cyano, or amido groups, or, if compatible with the reaction conditions, keto, formyl, or amino groups or other substituents. $R_5$ to $R_{12}$, independently, can be hydrogen, alkyl, aryl, or carbocyclic groups. In some cases, $R_6$ (or $R_7$) and $R_{12}$, $R_8$ and $R_9$, $R_{10}$ and $R_{11}$, or $R_8$ (or $R_9$) and $R_{10}$ (or $R_{11}$) can together form at least part of a ring. Preferably, at least one of $R_8$ to $R_{11}$ is an electron withdrawing group.

In another aspect, the invention features a method for identifying a compound that binds to a macromolecule. The method includes screening any of the above libraries for a characteristic that indicates bioactivity. For example, the compound can be a bioactive molecule (i.e., a molecule that affects the function of a target or that modulates the biological activity of a target, by, for example, upregulating or downregulating activity). The compound can also bind to a receptor or inhibit an enzyme.

In still another embodiment, the invention features a method for preparing a spiro[pyrrolidine-2,3'-oxindole] compound. The method includes reacting an isatin (e.g., an isatin of Table 1) with an α-amino acid (e.g., an α-amino acid of Table 2) to form an azomethine ylide; and reacting the azomethine ylide with a chalcone (e.g., a chalcone prepared from the reaction of an arylaldehyde of Table 3 and an acetophenone compound of Table 4) to form the spiro [pyrrolidine-2,3'-oxindole].

In another aspect, the invention features a spiro compound comprising the formula:

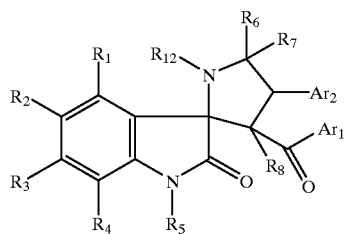

where $Ar_1$ and $Ar_2$ can be, independently, substituted or unsubstituted aryl or heteroaryl groups; $R_1$ to $R_4$, independently, can be hydrogen, alkyl, aryl, carbocyclic, fluoro, chloro, bromo, iodo, thio, hydroxyl, alkylthio, alkoxy, carboxy, sulfonyl, nitro, cyano, or amido groups, or, if compatible with the reaction conditions, keto, formyl, or amino groups or other substituents; and $R_5$ to $R_8$ and $R_{12}$, independently, can be hydrogen, alkyl, aryl, or carbocyclic groups. In some cases, $R_6$ (or $R_7$) and $R_{12}$ can together form at least part of a ring.

An "arylaldehyde" is a compound having the following general structural formula:

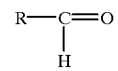

wherein R is covalently bound to the carbon atom. The "R" can be any aromatic group (i.e., phenyl or substituted phenyl) or heteroaromatic group (e.g., furyl or pyridyl or substituted variants thereof).

An "acetophenone compound" is a compound having the following general structural formula:

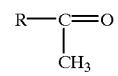

wherein R is covalently bound to the carbon atom. The "R" can be any aromatic or heteroaromatic group. Examples of acetophenone compounds include acetophenone, propiophenone, butyrophenone, and other acetophenone compounds listed in Table 4.

"Chalcones" are compounds having two aryl groups conjugated to each other through an α,β-unsaturated ketone. Thus, the parent chalcone has the structure: $Ar_1$—C(=O)—C(H)=C(H)—$Ar_2$. The aryl groups, $Ar_1$ and $Ar_2$, can be any substituted or unsubstituted aromatic or heteroaromatic groups.

A "library" is a collection of compounds (e.g., as a mixture or as individual compounds) synthesized from various combinations of two or more starting components (i.e., a combinatorial library). At least some of the compounds must differ from at least some of the other compounds in the library. A library can, for example, include 5, 10, 50, 100, 1,000, 10,000, 50,000, 100,000 or more different compounds (i.e., not simply multiple copies of the same compounds, although some compounds in the library may be duplicated or represented more than once). Each of the different compounds, whether they have a different basic structure or different substituents, will be present in an amount such that its presence can be determined by some means, e.g., can be isolated, analyzed, and detected with a receptor or suitable probe. The actual quantity of each different compound needed so that its presence can be determined will vary due to the actual procedures used and may change as the technologies for isolation, detection, and analysis advance. When the compounds are present in a mixture in substantially equimolar amounts, for example, an amount of 100 picomoles of each compound can often be detected. Preferably, the average purity of the compounds in the libraries of the invention is at least 70%, 85%, 90%, 95%, 99%, or higher.

Libraries can include both libraries of individual compounds (e.g., present substantially as a single compound-per-well, e.g., made via parallel synthesis) and mixtures containing substantially equimolar amounts of each desired compound (i.e., wherein no single compound dominates or is completely suppressed in any assay). Either library format can allow identification of an active compound discovered in an assay. Spatially arranged (or spatially addressable) array formats (see, e.g., U.S. Ser. No. 09/061,572, filed Apr. 16, 1998, and U.S. Pat. No. 5,712,171) can also be used to develop structure-activity relationships (SARs).

In this description, a "compound" can be a cyclic or an acyclic molecule, including, for example, carbon, hydrogen, nitrogen, and oxygen atoms, and possibly one or more other heteroatoms, including sulphur, phosphorus, halogens, metals, or other substituents.

Substituents on the organic compound can include one or more carbon, oxygen, hydrogen, iodine, bromine, chlorine, fluorine, nitrogen, sulfur, phosphorus, metal atoms, or any combination of these or other atoms. Typically, substituents can be attached to the isatins, amino acids, and dipolarophiles, and can include alkyls, alkenyls, alkynyls, and aryls, each of which may be either unsubstituted or substituted (e.g., as esters, carboxylic acids, nitriles, ethers, amides, and possibly aldehydes, ketones, or amines, where compatible with the reaction conditions), and may be cyclic, polycyclic, heterocyclic, or acyclic. The general structure of each of these groups is well known. Substituents can also be drawn from any other groups that can be bonded to an organic compound, for example, via a carbon, oxygen, or nitrogen atom.

A non-limiting list of examples of substituents includes hydrogen, hydroxy, $R_a$, $—OR_a$, $—NR_aR_b$, $—SO_{1,2,3,4}R_a$, $—C(O)R_a$, $—C(O)OR_a$, $—OC(O)R_a$, $—OC(O)OR_a$, $—NR_bC(O)R_a$, $—C(O)NR_aR_b$, $—OC(O)NR_aR_b$, $—NR_cC(O)NR_aR_b$, $—NR_bC(O)OR_a$, $—R_a—O—R_b$, $—R_a—NR_bR_c$, $—R_a—S—R_b$, $—R_a—S(O)—R_b$, $—R_a—S(O)_2—R_b$, $—OR_a—O—R_b$, $—NR_aR_b—O—R_c$, $—SO_{1,2,3,4}R_a—O—R_b$, $—C(O)R_a—O—R_b$, $—C(O)OR_a—O—R_b$, $—OC(O)R_a—O—R_b$, $—OC(O)OR_a—O—R_b$, $—NR_bC(O)R_a—O—R_c$, $—C(O)NR_aR_b—O—R_c$, $—OC(O)NR_aR_b—O—R_c$, $—NR_cC(O)NR_aR_b—O—R_d$, $—NR_bC(O)OR_a—O—R_c$, $—OR_a—S—R_b$, $—NR_aR_b—S—R_c$, $—SO_{1,2,3,4}R_a—S—R_b$, $—C(O)R_a—S—R_b$, $—C(O)OR_a—S—R_b$, $—OC(O)R_a—S—R_b$, $—OC(O)OR_a—S—R_b$, $—NR_bC(O)R_a—S—R_c$, $—C(O)NR_aR_b—S—R_c$, $—OC(O)NR_aR_b—S—R_c$, $—NR_cC(O)NR_aR_b—S—R_d$, $—NR_bC(O)OR_a—S—R_c$, $—OR_a—NR_bR_d$, $—NR_aR_b—NR_cR_d$, $—SO_{1,2,3,4}R_a—NR_bR_d$, $—C(O)R_a—NR_bR_d$, $—C(O)OR_a—NR_bR_d$, $—OC(O)R_a—N—R_bR_d$, $—OC(O)OR_a—NR_bR_d$, $—NR_bC(O)R_a—NR_cR_d$, $—C(O)NR_aR_b—NR_cR_d$, $—OC(O)NR_aR_b—NR_cR_d$, $—NR_cC(O)NR_aR_b—NHR_d$, and $—NR_bC(O)OR_a—NR_cR_d$; where $R_a$, $R_b$, $R_c$, and $R_d$ are each independently alkyl, alkenyl, alkynyl, aryl, aralkyl, aralkenyl, or aralkynyl groups having, e.g., 1 to 6, 10, 20, or even 30 carbon atoms. $R_a$, $R_b$, $R_c$ and $R_d$ can each be substituted, for example, with halo (e.g., 1 to 6 halogen atoms), nitro, hydroxyl, alkyl (e.g., having 1 to 6 carbon atoms), mercapto, sulfonyl, nitro, cyano, amino, acyl, acyloxy, alkylamino, dialkylamino, trihalomethyl, nitrilo, nitroso, alkylthio, alkylsulfinyl, or alkylsulfonyl. The substituents can include electron withdrawing groups, electron donating groups, Lewis acids, Lewis bases, as well as polar, nonpolar, hydrophilic, and hydrophobic functional groups.

An electron withdrawing group is a moiety that is capable of decreasing electron density in other parts of a compound to which it is covalently attached. Non-limiting examples of electron withdrawing groups useful in the invention include nitro, carbonyl, cyano, iodo, bromo, chloro, fluoro, and sulfone groups.

An electron donating group is a moiety that is capable of increasing electron density in other parts of a compound to which it is covalently attached. Non-limiting examples of electron donating groups useful in the invention include alkyl, amine, hydroxyl, and alkoxy.

Examples of substituents also include aliphatic (e.g., alkyl or alkenyl), alicyclic (e.g., cycloalkyl or cycloalkenyl), or aromatic (e.g., phenyl or naphthyl) substituents, aliphatic and alicyclic-substituted aromatic nuclei (e.g., p-(n-butyl)-phenyl or o-xylyl), as well as cyclic substituents wherein the ring is completed through another portion of the molecule (i.e., for example, any two indicated substituents can together form an alicyclic radical).

Hetero substituents are also contemplated. These are substituents that contain an atom or atoms other than carbon in a ring or chain otherwise composed of carbon atoms. Suitable heteroatoms include, for example, sulfur, oxygen, and nitrogen. Hetero substituents therefore include groups such as epoxides, ethers, pyridines, piperazines, furans, pyrrolidines, and imidazoles.

"Alkyl groups" should be construed to include both linear chain and branched chain derivatives of any substituted or unsubstituted acyclic carbon-containing moieties, including alkanes, alkenes, and alkynes. Alkyl groups having one to five, ten, twenty, or even more carbon atoms are possible. Examples of alkyl groups include lower alkyls, for example, methyl, ethyl, n-propyl, iso-propyl, n-butyl, iso-butyl, tert-butyl; higher alkyls, for example, octyl, nonyl, and decyl; lower alkenyls, for example, ethenyl, propenyl, propadienyl, butenyl, butadienyl; higher alkenyls such as 1-decenyl, 1-nonenyl, 2,6-dimethyl-5-octenyl, and 6-ethyl-5-octenyl; and alkynyls such as 1-ethynyl, 2-butynyl, and 1-pentynyl. Other linear and branched alkyl groups are also within the scope of the present invention.

In addition, such alkyl groups can also contain various substituents in which one or more hydrogen atoms has been replaced by a functional group. Functional groups include, but are not limited to, tertiary amine, amide, ester, ether, and halogen, i.e., fluorine, chlorine, bromine and iodine. Specific substituted alkyl groups can be, for example, alkoxy such as methoxy, ethoxy, butoxy, and pentoxy; dimethylamino, diethylamino, cyclopentylmethylamino, benzylmethylamino, and dibenzylamino; formamido, acetamido, or butyramido; methoxycarbonyl or ethoxycarbonyl; or dimethyl or diethyl ether groups.

"Carbocyclic groups" include both substituted and unsubstituted, cyclic, carbon-containing moieties such as cyclopentyl, cyclohexyl, cycloheptyl, and adamantyl. Such cyclic groups can also contain various substituents in which one or more hydrogen atoms have been replaced by a functional group. Such functional groups include those described above, as well as lower alkyl groups as described above. The cyclic groups of the invention can also include one or more heteroatoms, for example, to form heterocyclyls.

"Aryl groups" include substituted and unsubstituted hydrocarbon rings bearing a system of conjugated double bonds, usually comprising (4n+2) pi bond electrons, where n is zero or a positive integer. Examples of aryl groups include, but are not limited to, phenyl, naphthyl, anisyl, tolyl, xylyl and the like. Aryl groups can also include aryloxy, aralkyl, aralkyloxy and heteroaryl groups, e.g., pyrimidine, morpholine, piperazine, piperidine, benzoic acid, toluene, thiophene, and the like. These aryl groups can also be substituted with any number of a variety of functional groups. In addition to the functional groups described above in connection with substituted alkyl groups and carbocyclic groups, functional groups on the aryl groups can also include other nitrogen, oxygen, sulfur, or halogen bearing groups.

It is to be understood that this invention is not limited to the particular compounds and their substituents described herein; such compounds and their substituents, as well as the methods used in their manufacture and use, can, of course, vary. Also, many of the compounds of the new libraries, compounds produced by the new methods, and compounds shown in the figures can exist in two or more stereoisomeric forms. Unless specifically stated otherwise herein, the invention should be understood to include all stereoisomeric permutations of these compounds.

Throughout this description and the claims, it must be noted that the singular forms "a," "an," and "the" include plural referents unless the context clearly dictates otherwise. Thus, for example, reference to "an organoboronic acid" or "a benzylic amine" includes groups or subgroups of organoboronic acids or benzylic amines. Similarly, reference to "solvent" includes reference to mixtures of solvents, and reference to "the method" includes a plurality of methods.

The present invention includes a variety of different aspects, including novel acyclic, cyclic, and heterocyclic organic compounds, libraries of such compounds, and processes for synthesizing such compounds and libraries thereof. Further, within each of these aspects of the invention, the present invention includes a number of specific embodiments. The invention provides processing technology to produce and isolate compounds and libraries of compounds, one or more of which can mimic the activity or characteristics of naturally-occurring molecules or synthetic biologically active molecules, but which compounds can have different chemical structures as compared to the natural molecule or synthetic molecule. The word "mimic" is used loosely, in that the compounds produced can have the same activity, greater activity, or lesser activity than naturally occurring molecules or biologically active synthetic molecules, or can block the activity of these molecules entirely. Furthermore, the compounds can have similar or radically different structures compared to naturally occurring molecules.

The methods described herein can be used to create libraries of compounds that differ from the specific libraries described below, but which are also within the scope of the invention.

The term "dipolarophile" is used herein to describe any compound that can react with an azomethine ylide in a [3+2] fashion. For example, activated olefins (e.g., olefins substituted with at least one electron withdrawing group, such as chalcones, acrylates, fumarates, maleates, maleimides, cinnamates, cinnamonitriles, nitroolefins, acrylonitriles, vinyl sulfones, vinyl oxindoles, and vinyl sulfoxides) can be suitable dipolarophiles.

"Isatins" are cyclic α-ketoamides having an aryl group to which a five-member ring is fused. "Fused" rings have two atoms in common. In an isatin, two of the remaining three ring members are the carbon atoms of carbonyl (>C=O) groups, and the third remaining member is the nitrogen of the amide. In general, isatins have the structure:

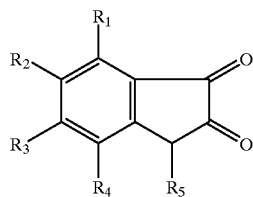

where $R_1$ to $R_4$, independently, can be hydrogen, alkyl, aryl, carbocyclic, fluoro, chloro, bromo, iodo, thio, hydroxyl, alkylthio, alkoxy, carboxy, sulfonyl, nitro, cyano, or amido groups, or, if compatible with the reaction conditions, keto, formyl, or amino groups or other substituents; and $R_5$ can be hydrogen, alkyl, aryl, or carbocyclic groups.

"α-Amino acids" include a carboxylic acid group (—C(=O)—OH) and an amino group (—N($R_{13}$)($R_{14}$); where $R_{13}$ and $R_{14}$ can be, independently, hydrogen or another substituent), separated by a single methylene moiety (—C($R_{15}$)($R_{16}$)—; where $R_{15}$ and $R_{16}$ can be, independently, hydrogen or another substituent).

A "spiro compound" is an organic compound or moiety that has a structure including two closed rings where the two rings have a single carbon atom in common with each other. The compound can be saturated or unsaturated. A spiro compound can be mono-, bi-, tri-, or polycyclic depending on the number of rings present; the three major groups of cyclic compounds include: (1) alicyclic, (2) aromatic (also called arene) and (3) heterocyclic. Spiro[pyrrolidine-2,3'-oxindole] is a spiro compound.

A "retrievable amount" is an amount of a compound in a library that is present in a concentration such that the compound can be separated from the other compounds of the library (i.e., in the case of mixtures) by standard techniques. Preferably, at least 50 or 100 pmol, of a compound is present in a library when the compounds of the library are present in approximately equimolar amounts.

An "analyzable amount" is an amount of a compound that is present in a library such that the compound can be detected and identified in the library. At least approximately 10 pmol, more preferably 50 pmol of a compound should be present in the library when the components of the library are present in approximately equal molar amounts.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

Advantages of the new methods and libraries include incorporation of a plurality of diversity elements in a single step. A diversity element is any part of a compound that varies among the members of a library. The amino acid components can introduce at least two diversity elements, for example, one at the α-side chain and one as a substituent on the amino group. The isatins can also be N-substituted in addition to having a substituent or substituents on the aromatic ring, thus incorporating two diversity elements. Finally, the chalcones can have independent substituents on their two aromatic rings, also introducing up to two diversity elements.

It should be noted that not all of these diversity elements are varied in every library (or member of the library) of the invention. For example, a library can be made wherein the substitution at the nitrogen of the isatin is constant in all the members in the library. Additional diversity elements can also be introduced; for example, the aryl groups of the chalcone can be based on a variety of heteroaromatic groups (each of which can be substituted) rather than simply being a phenyl group.

The new libraries allow exploration of structure-activity relationships based on the interactions between the compounds in the library and natural receptor sites.

Another advantage of the present invention is that the new methods can allow rapid, simultaneous synthesis of a vast number of independent compounds in greater than 50%, 75%, or even 85% yield in some cases. Such high yields, although not a critical feature of the present libraries and methods, can allow preparation of libraries of substantially pure individual compounds without the need for extensive purification (e.g., a single compound-per-well). For certain applications, impurities can be highly detrimental. For example, agrichemicals are often used in large quantities and a substantial impurity in such chemicals can have undesired side effects. However, even low yielding reactions or reactions that produce significant amounts of impurities can be used in the new methods (e.g., followed by some purification, or if libraries containing mixtures of compounds are suitable).

In the single compound-per-well format, each well or reaction vessel contains a predominant species. It is not necessary that the predominant species be 100% pure; all that is required is that the predominant species be pure enough that structure-activity relationships can be reliably probed in a primary screen without the need for additional deconvolution. Although in some cases, the interaction of the predominant species with an impurity can result in false positive or false negative results, a small amount of impurity is often tolerable.

New (i.e., second generation) libraries can be constructed based on the structure-activity relationships derived from a primary screen. Structure-activity relationships found in the second generation screens can in turn serve as the basis for construction of subsequent generations of libraries. Through such an iterative process, it is possible to rapidly implement lead optimization strategies and to confirm or supplant existing theories or assumptions regarding binding (see, e.g., Zambias et al., U.S. Pat. No. 5,712,171). These methods can themselves result in compounds having the same or stronger affinity for a natural receptor site as a natural or known bioactive compound that ordinarily binds the same site. The methods can also result in compounds with superior properties relating to absorption, distribution, metabolism, toxicity, or stability.

Pharmaceutically active compounds are often highly substituted heterocycles; there is therefore a need for a method to rapidly synthesize a large number of related substituted heterocyclic compounds quickly and relatively inexpensively. The present methods overcome the problem of a separate synthesis for each member of a group of candidate compounds where the structural components conferring biological activity are unknown.

Other features and advantages of the invention will be apparent from the following detailed description, and from the claims.

DETAILED DESCRIPTION

Figure 1:
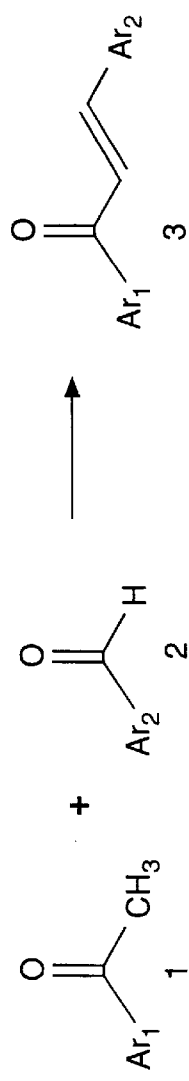
FIG. 1 is a schematic drawing showing the synthesis of substituted trans-chalcones.

The invention features new libraries of spiro[pyrrolidine-2,3'-oxindoles], methods of making these libraries, and methods of using these libraries to assay for activity. The libraries and methods can be used, for example, in the discovery of drugs for use in the treatment of cancer, immune disorders, and inflammation, as well as in agricultural biology applications, in bioseparations, and in the development of other types of pharmaceuticals. New drugs discovered via the methods of the invention can include, for example, new kinase inhibitors (e.g., screened using the methods described in Mohammadi et al., *Science*, 276:955–960, 1997, references cited therein, and in U.S. Pat. No. 5,656,654).

General Methodology

The common features of the synthetic methods will first be described.

In general, the methods of the invention feature the reaction of an isatin, an amino acid, and a dipolarophile. In accordance with the present invention, various methodologies can be applied for the production of libraries. For example, by combining the reagents in stoichiometric quantities and applying the new methods such that each reaction is driven to substantial completion where plausible, each reaction product can be produced in a predictable and defined amount and in an amount sufficient such that the compounds can be retrieved and analyzed. The resulting amount of each of the compounds is predictable insofar as the amount of starting material used in each reaction is controlled.

In certain embodiments of the invention, one or more isatins are reacted with one or more α-amino acids to form one or more highly reactive azomethine ylides, which are then stereo- and regio-selectively trapped by reaction with one or more trans-chalcones (e.g., trans-chalcones previously prepared from one or more arylaldehydes and one or more acetophenone compounds) or other dipolarophiles. The reactions are carried out under appropriate time (for example, 0.5 to 24 hours, e.g., 8 to 12 hours) and temperature conditions (for example, 60 to 95° C., e.g., 80 to 850° C.) in an appropriate solvent (i.e., a solvent in which the reaction components are soluble, e.g., dioxane, methanol, aqueous methanol, aqueous tetrahydrofuran, or mixtures thereof; one equivalent of a base such as sodium hydroxide can be added to aid dissolution of the amino acid). Alternatively, the methods can be carried out on a solid support, wherein at least one of the reagents is supplied in an immobilized format.

In preparing the libraries, the reaction of each of the plurality of isatins with each of the plurality of amino acids can be carried out, followed by reaction of the resulting azomethine ylides with each of the plurality of dipolarophiles (i.e., to create an exhaustive library that includes every permutation of compounds that can be prepared from the particular staring components). Alternatively, some of the plurality of isatins can be reacted with some of the plurality of amino acids, and some of the resulting azomethine ylides can be reacted with some of the dipolarophiles. Other isatins can be reacted with the same or different isatins, or both, then with some of the dipolarophiles, thereby producing a library that contains less than all of the possible permutations.

Non-limiting lists of examples of suitable isatins, α-amino acids, arylaldehydes, and acetophenone compounds are provided in Tables 1, 2, 3, and 4, respectively.

TABLE 1

| Isatins |
| --- |
| 5-fluoroisatin |
| isatin |
| 1-methylisatin |
| 5-methylisatin |

TABLE 1-continued

Isatins 5-nitroisatin
5-iodoisatin
1-phenylisatin
5-chloro-7-methylisatin
5,7-dimethylisatin
5-bromoisatin
5-chloroisatin
5-trifluoromethoxyisatin
1-benzylisatin
1-(3-chlorobenzyl)isatin
1-(4-methoxybenzyl)isatin
1-allylisatin

TABLE 2

α-Amino Acids sarcosine
L-valine
L-methionine
L-methionine sulfoxide
L-methionine sulfone
L-alanine
L-glutamine
L-threonine
D-serine
L-phenylalanine
glycine
L-leucine
O-benzyl-(D,L)-serine
O-methyl-L-tyrosine
L-isoleucine
L-proline
4-hydroxy-L-proline
R-thiazolidine carboxylic acid
L-tryptophan
L-phenylglycine

TABLE 3

Arylaldehydes 2-furaldehyde
3-(4-t-butylphenoxy)benzaldehyde
3-(3-trifluoromethylphenoxy)benzaldehyde
3-(4-methylphenoxy)benzaldehyde
3-(3,4-dichlorophenoxy)benzaldehyde
3-bromobenzaldehyde
3-furaldehyde
5-ethyl-2-furaldehyde
5-methylfurfural
4-ethylbenzaldehyde
2,5-dimethylbenzaldehyde
2-thiophenecarboxaldehyde
3-thiophenecarboxaldehyde
4-bromo-2-thiophenecarboxaldehyde
4-n-butoxybenzaldehyde
3,4-dichlorobenzaldehyde
m-anisaldehyde
4-isopropylbenzaldehyde
4-propoxybenzaldehyde
3-methyl-p-anisaldehyde
6-methyl-2-pyridinecarboxaldehyde
1,4-benzodioxan-6-carboxaldehyde
5-methyl-2-thiophenecarboxaldehyde
benzaldehyde
3-(4-methoxyphenoxy)benzaldehyde
3,5-dimethoxybenzaldehyde
4-t-butylbenzaldehyde
3,4-dimethoxybenzaldehyde
3-phenoxybenzaldehyde
4-bromobenzaldehyde TABLE 3-continued Arylaldehydes o-tolualdehyde
3-fluoro-p-anisaldehyde
2,6-difluorobenzaldehyde
4-ethoxybenzaldehyde
4-fluorobenzaldehyde
2,4-dichlorobenzaldehyde
4-chlorobenzaldehyde
4-phenoxybenzaldehyde
m-tolualdehyde
p-tolualdehyde

TABLE 4

Acetophenone Compounds acetophenone
3'-methylacetophenone
4'-methylacetophenone
3',4'-dimethylacetophenone
4'-ethylacetophenone
4'-t-butylacetophenone
4'-cyclohexylacetophenone
3'-methoxyacetophenone
4'-methoxyacetophenone
4'-ethoxyacetophenone
3',4'-dimethoxyacetophenone
2'-methylacetophenone
4'-n-butylacetophenone
2-acetyl-5-methylfuran
2-acetylfuran
2-acetyl-1-methylpyrrole
2-acetyl-3-methylthiophene
2'-trifluoromethylacetophenone
2'-fluoro-6'-trifluoromethyl-acetophenone
2',4',6'-trimethylacetophenone
2'-methoxyacetophenone
2',4'-dimethoxyacetophenone
2',5'-dimethoxyacetophenone
2',6'-dimethoxyacetophenone
2'-fluoro-4'-methoxyacetophenone
2',3',4'-trimethoxyacetophenone
4'-chloroacetophenone
1,4-benzodioxan-6-yl methyl ketone
4'-morpholinoacetophenone
4'-piperidinoacetophenone
3',4'-methylenedioxyacetophenone
3',5'-dimethoxyacetophenone Preparation of Trans-Chalcones FIG. 1 illustrates a general scheme for the preparation of trans-chalcones 3 from arylaldehydes 2 and acetophenone compounds 1 via the aldol condensation reaction (Kohler et al., *Org. Syn.*, Vol. 1, page 78, 1941). In general, the chalcone-forming aldol condensation is carried out at ambient temperature (e.g., 20 to 35° C.) in a mixture of ethanol and water (e.g., in a ratio of 1:1 to 10:1, e.g., about 4:1) or other aqueous alcohol (e.g., 4:1 methanol and water) with one equivalent of sodium hydroxide or other base added. The reactions are typically stirred overnight (e.g., 0.5 to 24 hours, or 8 to 12 hours), during which time the reaction products precipitate out of the solution. The products are then isolated by filtration. The filtered products can be purified prior to further use, for example, by recrystallizing from ethanol.

Diversity elements can be introduced into the chalcones through either the arylaldehyde 2 or the acetophenone compound 1, or both. For example, the aryl group of the arylaldehyde can be a substituted phenyl (e.g., chlorophenyl, nitrophenyl, anisyl, salicylyl, anthranilyl, or xylyl), a 5-member heterocyclic group (e.g., 2-thienyl, 3-furyl, 5-imidazolyl, or 2-pyrrolyl, or substituted variants thereof such as 5-bromo-4-oxazolyl or picolyl), or a 6-member heterocycle (e.g., pyridyl or pyrimidyl). Other representative arylaldehydes are listed in Table 3. Similarly, the acetophenone compound can be a methyl ketone of any aromatic group such as 3'-methyl acetophenone, 3'-chloro-2'-ethoxy-5'-methylacetophenone, or 2-acetyl-3-nitrothiophene. Additional examples of suitable acetophenone compounds are listed in Table 4. The use of homologs of acetophenones such as propiophenones and butyrophenones is also within the scope of the invention.

Formation of Reactive Azomethine Ylide Moieties

Figure 2:
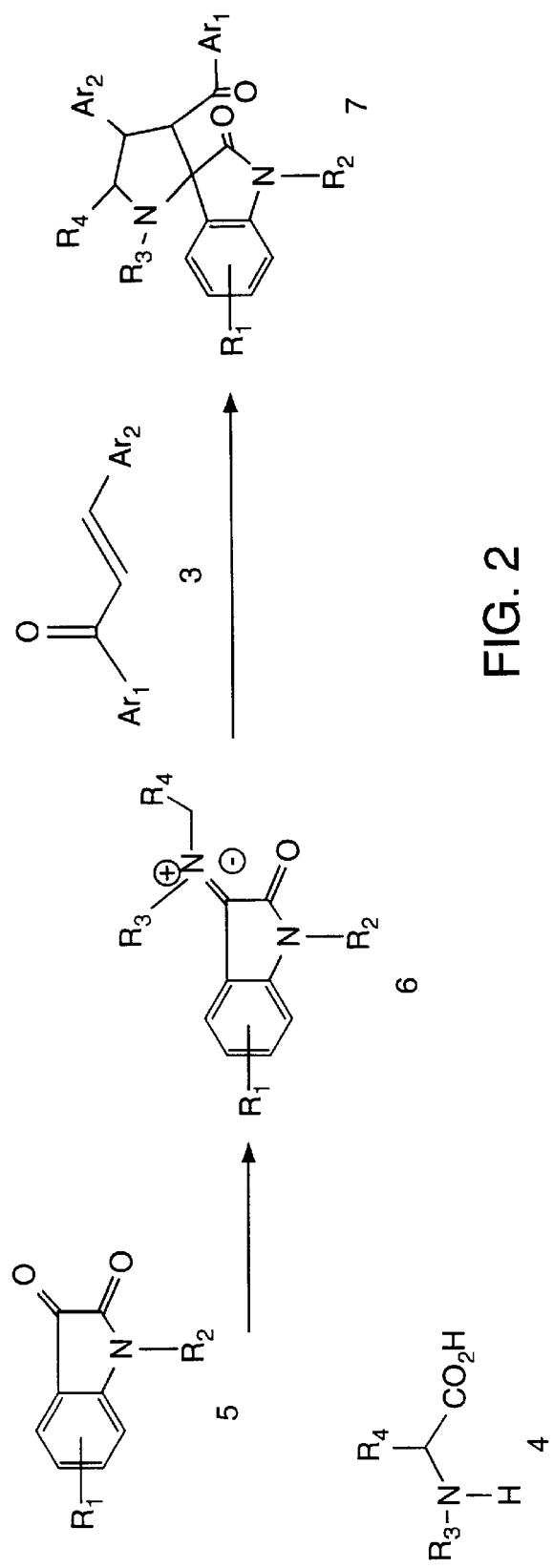
FIG. 2 is a schematic drawing showing the general synthesis of new spiro[pyrrolidine-2,3'-oxindoles].

The α-carbonyl moiety of α-ketoamides (e.g., isatins) is highly reactive toward α-amino acids. The first step in the general reaction scheme of FIG. 2 illustrates this reaction. Upon heating the α-amino acids 4 to a temperature sufficient for decarboxylation (e.g., 80–90° C.) in the presence of an isatin 5, for example, a reactive azomethine ylide 6 is formed. The ylide-forming reaction can be carried out in a mixture of dioxane and water (e.g., in a ratio of 1:1 to 4:1, or about 3:1) or other polar solvent mixture.

Numerous α-amino acids can be used to introduce diversity into the new libraries. For example, naturally occurring α-amino acids (e.g., L-alanine, L-proline, or D-glutamine), as well as other α-amino acids (e.g., 4-hydroxy-L-proline, R-thiazolidine carboxylic acid, or L-ornithine) can be used in the reaction. Table 2 lists additional α-amino acids. A large number of suitable α-amino acids are commercially available from vendors such as Aldrich, Nova Biochem, and Sigma.

The isatin component can also introduce diversity by variation of the $R_1$ and $R_2$ groups on the isatin ring system 5. For example, isatin itself (i.e., $R_1=R_2=H$) can be used, as can any substituted isatins (e.g., 1-(3-bromobenzyl)benzylisatin, 1-allylisatin, or 5,6-diethylisatin. A number of other isatins are listed in Table 1. Other variants of isatin can be purchased, for example from Aldrich, or can be made via known methods (see, e.g., Marvel et al., *Org. Syn.*, Vol. 1, page 327, 1943). Additionally, similar reactive compounds such as cyclic α-diketones and other cyclic α-ketoamides can be substituted for isatins to further expand the diversity of the new libraries.

1,3-Cycloaddition of the Azomethine Ylides to the Trans-Chalcones

As shown in FIG. 2, the azomethine ylide 6 reacts with the trans-chalcone 3 to generate a spiro[pyrrolidine-2,3'-oxindole] 7. The chalcone 3 is generally added simultaneously with the α-amino acid 4 and the isatin 5. Thus, the azomethine ylide 6 can be transiently generated in situ and trapped immediately by reaction with the chalcone 3. This reaction proceeds in the same polar solvent as the ylide formation reaction.

If cyclic α-amino acids such as proline, thiaproline, or 4-hydroxyproline are used as precursors, the resulting products will have an additional ring incorporated into the structure. In the case of the proline derivatives, for example, the products are spiropyrrolizidines.

The size of the library (i.e., the number of individual compounds that make up the library) is limited only by the number of different arylaldehyde, acetophenone compound, α-amino acid, and isatin starting materials used as precursors. For example, a library formed from the 16 isatins listed in Table 1, the 20 α-amino acids in Table 2, the 40 arylaldehydes of Table 3, and 32 acetophenone compounds presented in Table 4 would include 16×20×40×32=409,600 distinct compounds if the entire library were synthesized.

Since the number of known isatins, α-amino acids, arylaldehydes, and acetophenone compounds vastly exceeds the number chosen for illustrative purposes in Tables 1–4, much larger libraries and sets of different libraries can be created according to the methods described herein.

The creation of the new libraries can be partially or fully automated. For example, robotic pipetting devices can be used to introduce the relevant molecular components, reagents, solvents, and catalysts into the reaction vessels, and conditions such as temperature can be controlled electronically via a computer. Such a computer can also keep track of the location and identity of all of the compounds present in each library. Automation can greatly accelerate the creation and screening of the libraries.

Preparation of Other Dipolarophiles

Figure 3:
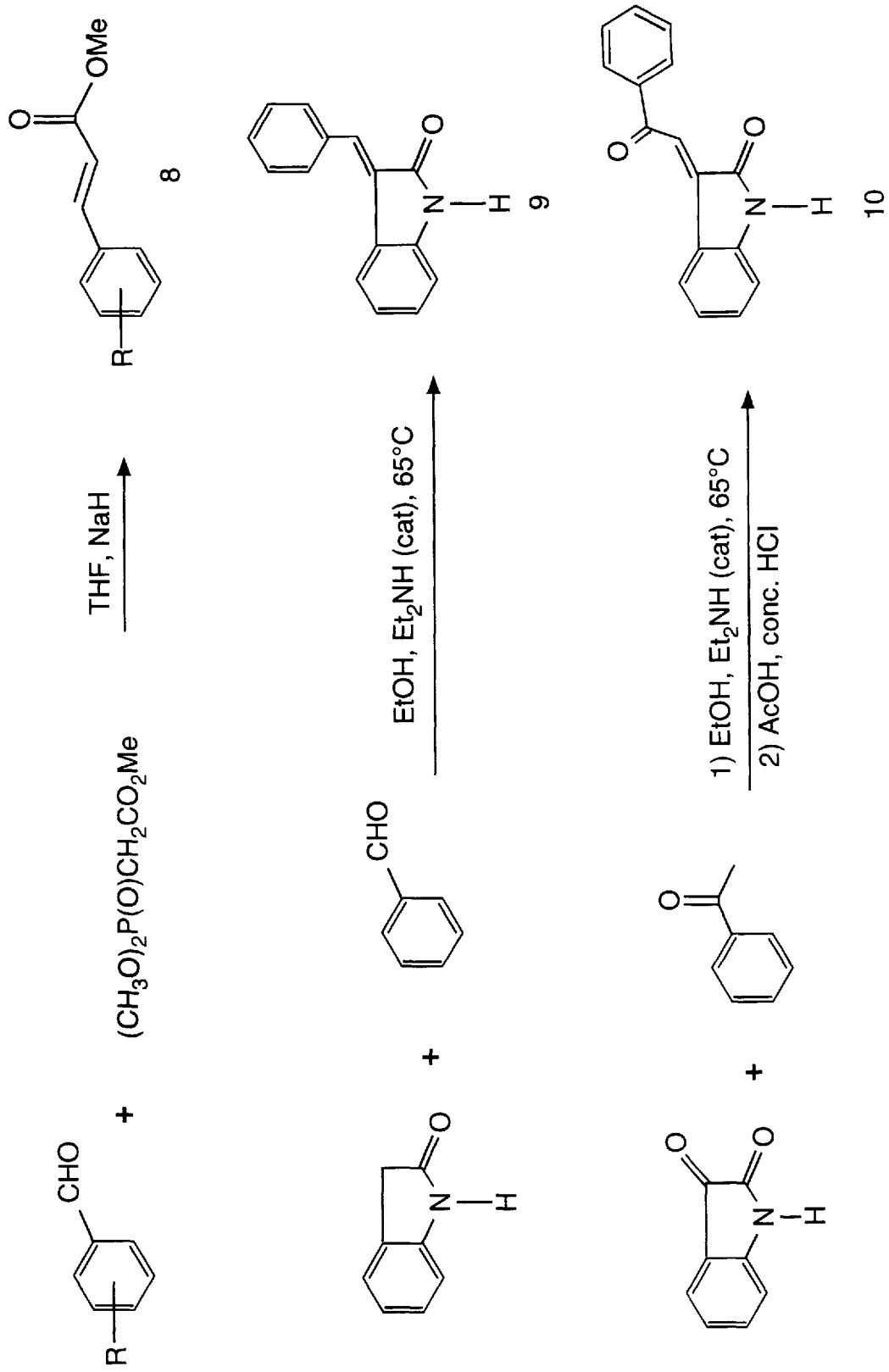
FIG. 3 is a schematic drawing showing the synthesis of acrylate esters (i.e., cinnamate esters 8) and vinyl oxindoles 9 and 10.

Synthetic schemes for the preparation of acrylate esters (e.g., cinnamate ester 8) and vinyl oxindoles (e.g., arylidene oxindole 9, or vinyl oxindole 10) are shown in FIG. 3. For example, isatins can be condensed with ketones to produce tri- or tetrasubstituted vinyl indoles. Alternatively, base-promoted condensation of an oxindole with an aldehyde can be used to prepare vinyl oxindoles. Certain oxindoles are commercially available; others can be produced by reduction of an isatin (e.g., see Table 1) to an oxindole (see e.g., *Synth. Commun.* 24, 2835, 1994).

1,3-Cycloaddition of the Azomethine Ylides to Vinyl Oxindoles

Figure 4:
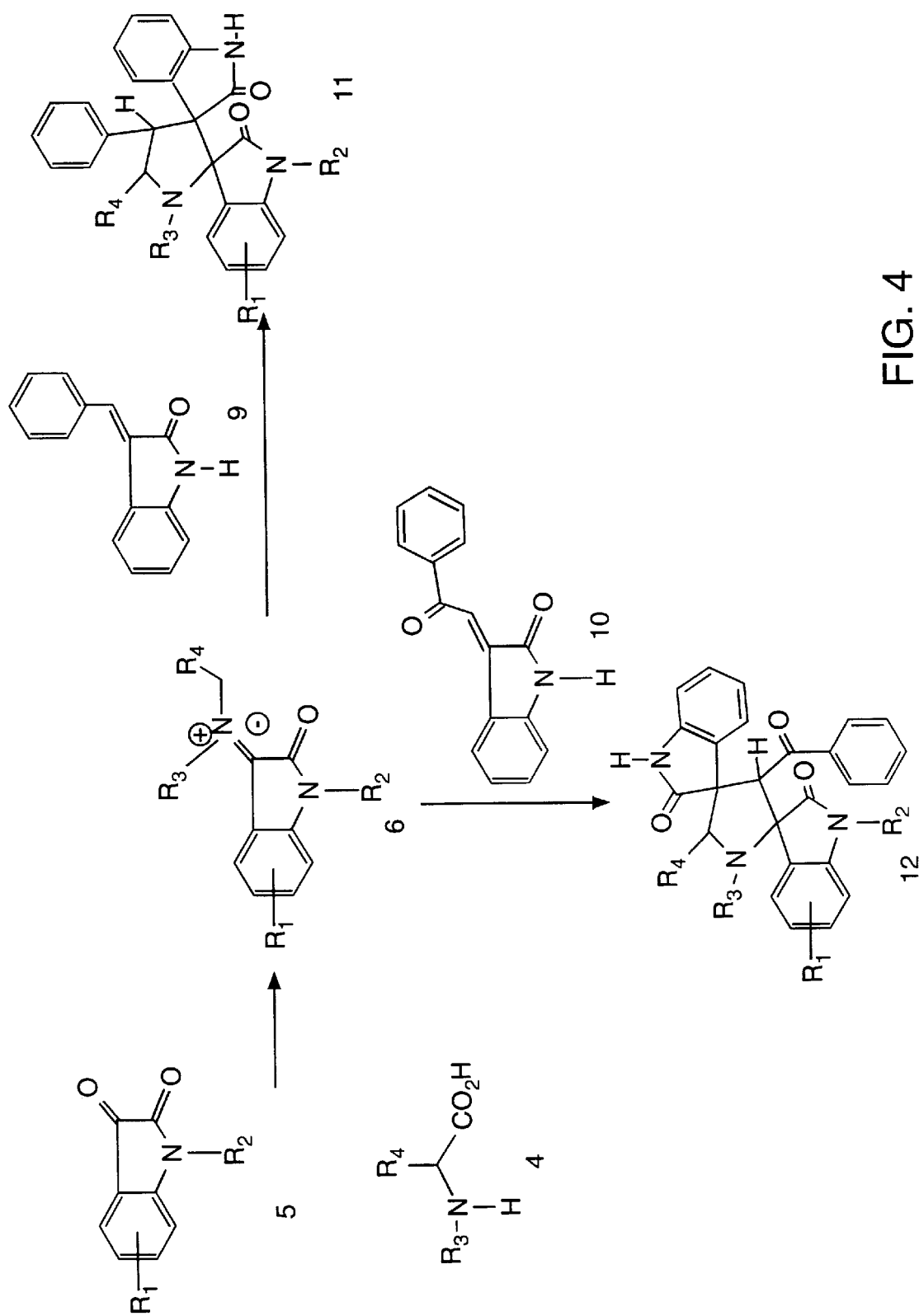
FIG. 4 is a schematic drawing showing the synthesis of two spiro-spiropyrrolidines.

As shown in FIG. 4, spiro-spiropyrrolidines can be formed by reacting azomethine ylides 6 with vinyl oxindoles 9 or 10. The reaction of vinyl oxindole 9 works well with secondary amino acids such as sarcosine, proline, and thiaproline. The reaction does not work well with primary amino acids under the reaction conditions used for the condensation with secondary amino acids. The reaction of vinyl oxindole 10 works well with either primary or secondary amino acids.

Application of Single Compound-Per-Well Methodology

Numerous strategies can be employed for determining the identity of a specific compound in a library. One such strategy is the single compound-per-well method. In this method, only one member of each class of starting components (i.e., one isatin, one α-amino acid, and one chalcone) is added to each of many reaction vessels (e.g., test tubes, vials, wells of 96-well plates, or sample plates). Thus, each vessel ends up containing predominantly a single spiro [pyrrolidine-2,3'-oxindole]. If the identity of the components that went into each vessel is carefully tracked, for example, by marking the vessel with a code, then the structure of the oxindole product can be rapidly ascertained. Other strategies of identifying specific members of the libraries would be known to one of ordinary skill in the art. For example, identification by spatial address, identification by detection of a tag (e.g., a fluorescent, radioactive, or colored tag), labelling of reaction vessels with radiotransmitters, and direct determination (e.g., by nuclear magnetic resonance, mass spectroscopy, or infrared spectroscopy) are all suitable methods that can be used in conjunction with the present methods and libraries.

A particularly straightforward example is provided, for instance, by a library made from 12 isatins, 8 amino acids, and 20 chalcones. This library is prepared by obtaining 20 96-well plates and numbering them from 1 to 20. The first chalcone is loaded into every well of the first plate, the second chalcone is loaded into every well of the second plate, and so on. The first isatin is loaded into each of the wells in the first of the twelve rows of wells on each plate, the second isatin in the wells of the second rows, etc. Finally, the α-amino acids are similarly loaded into the wells in the columns of the plates.

After assaying each of the wells of the 20 plates for some characteristic (e.g., fluorescence, binding to a ligand, or biological activity) the identity of the compound in each well of interest can be quickly determined. For example, the compound in column 7, row 2 of plate #18 would clearly be the spiro[pyrrolidine-2,3'-oxindole] produced from the reaction of the seventh amino acid, the second isatin, and the eighteenth chalcone. The structure of this oxindole is readily deduced, provided that the identity of each of the starting components is known.

Utility of the New Libraries

The new libraries can be used for any application for which it would be useful to screen multiple compounds. For example, the libraries can be used in screening for affinity ligands for use in bioseparations. The libraries can also find utility in screening assays for compounds of use in the pharmaceuticals or agricultural industries. For example, the libraries can be assayed for the discovery of new drugs, herbicides, or pesticides.

Assays for Activity

To most efficiently probe the binding region of a receptor protein or other molecule, it is generally preferred to create a library of compounds having a variety of substitutions and/or ring structures. A greater variety of structures in a library increases the chance of identifying a compound having desired binding properties. By applying the methods described herein to the synthesis of a collection of compounds, one can prepare a large group of compounds for screening. For example, one can prepare a library having a variety of substituents for analysis of, e.g., relative receptor binding affinities. The library can be small (approximately 10 different compounds) or large (more than 10,000, or even 100,000 or 200,000 different compounds).

Such libraries are useful for identifying analogs to a naturally occurring bioactive peptide or other molecule which binds with a requisite affinity to the appropriate receptor. For example, to identify a compound that binds to a known cell-surface receptor, one can prepare a culture of cells expressing the cell-surface receptor, apply the library under conditions conducive to binding, and determine the degree to which members of the library bind the cell-surface receptor or elicit a receptor response.

Examples of specific assays that can be used for probing the new libraries for biological activity include screens against proteolytic enzymes in pathogens, screens used to identify thrombin, plasmin, or trypsin inhibitors, screens used to identify inhibitors of tumor necrosis factor (TNF) convertase, screens used to identify inhibitors of angiotensin converting enzyme (ACE), and screens to identify useful ligands for bioseparations. In one embodiment, the compounds are screened in a format in which the compounds are logically ordered in a spatially arranged array according to the methods described in U.S. Pat. No. 5,712,171. These methods can generate a pattern of activity data, providing structure-activity relationship information that can facilitate optimization of active compounds.

In one example, the natural substrate of an enzyme can be labelled with a fluorescent, radioactive, or colored tag that is detectable upon cleavage from the substrate by the normal functioning of the enzyme. By comparing the level of detected cleavage in a control sample (i.e., containing the enzyme and substrate but no compounds from the libraries) with that in samples incubated with members of the new libraries, it can be determined whether any of the compounds in the libraries inhibit or enhance the activity of the enzyme. If less cleavage is detected in a particular sample, for example, the compound is an inhibitor. The compounds can be screened at various concentrations (e.g., from 1 pM to 1 mM, or from 1 to 10 $\mu$M). Generally, any compound that decreases the activity of the enzyme by more than 50% is considered to be an inhibitor, although for certain applications greater inhibition (e.g., 80%, 95%, 99%, or even nearly 100%) is more desirable.

The assay procedures can be automated. For instance, a robot can be used to remove an aliquot of each member of a new library and combine the aliquot with an assay sample. Automated fluorescence detectors or other automated laboratory devices can then be used to identify particular characteristics.

EXAMPLES

The following examples provide specific methods of making and using the compounds and libraries of the invention and do not limit the scope of the invention. Other functional groups can be attached to the cyclic compounds and subjected to known types of reactions to increase the diversity of the libraries.

Example 1

Preparation of a Library of Spiro[pyrrolidine-2,3'-oxindoles]

Experimental Conditions

Each of the arylaldehydes listed in Table 3 was independently combined with each of the acetophenone compounds listed in Table 4 in a 4:1 mixture of ethanol and water. One equivalent of sodium hydroxide was added to each of the resulting reaction mixtures. The reaction mixtures were stirred at 25° C. for 12 hours, and the chalcones precipitated from the mixtures. The chalcones were isolated by filtration and recrystallized from ethanol.

200 $\mu$l (50 $\mu$mol) of a 0.25 M solution of each of the isatins listed in Table 1, in dioxane; 200 $\mu$l (50 $\mu$mol) of a 0.25 M solution of the $\alpha$-amino acids listed in Table 2, in water (including 1 equivalent of sodium hydroxide for the L-phenylalanine, L-leucine, O-benzyl-(D,L)-serine, L-tryptophan, L-isoleucine, and O-methyl-L-tyrosine); and 400 $\mu$l (50 $\mu$mol) of a 0.125 M solution containing the chalcones produced by reaction of the arylaldehydes and acetophenone compounds of Tables 3 and 4, in dioxane, were combined in 1 ml perfume vials. The vials were capped and heated at 80° C. overnight. The solvent was then evaporated under reduced pressure and the resulting products were all recovered in greater than 85% purity according to high pressure liquid chromatography (HPLC) and mass spectroscopy (MS) experiments.

Characterization of the Libraries

Proton nuclear magnetic resonance ($^1$H-NMR) spectra were collected at 300 MHz in deuterated chloroform on a Varian NMR. Chemical shifts for the NMR spectra are reported in ppm from tetramethylsilane (TMS) as an internal standard.

Mass spectra were collected using a Fisons spectrometer under electrospray (ES+) conditions. HPLC analysis was carried out on a BETASIL™ C-18 basic column using an acetonitrile-water gradient with 0.1% trifluoroacetic acid (TFA). The HPLC peaks detected with a UV ($\lambda$=254 nm) detector or an evaporative light scattering detector (ELSD).

For example, the spiropyrrolizidines derived from reaction of L-proline, L-thiaproline, and 4-hydroxy-L-proline, individually, with unsubstituted chalcone and unsubstituted isatin were analyzed. The spiropyrrolizidine derived from reaction of L-proline with unsubstituted chalcone and 5-bromoisatin was also analyzed. The results follow. The three-dimensional structures of the compounds were proved by single crystal X-ray crystallography.

The first spiropyrrolizidine (i.e., derived from L-proline) was isolated as a yellow oil of 98% purity. The calculated mass for $C_{27}H_{24}N_2O_2$ is 408; ES+ MS yielded a mass of 409, as expected for the ionized fragment made up of the molecule and a proton (M+H+).

The second spiropyrrolizidine (i.e., derived from L-thiaproline) was isolated as a yellow oil of 97% purity. The calculated mass for $C_{26}H_{22}N_2O_2S$ is 426; ES+ MS yielded a mass of 427, as expected for M+H+.

The third spiropyrrolizidine (i.e., derived from 4-hydroxy-L-proline) was isolated as a yellow oil of 94% purity. The calculated mass for $C_{27}H_{24}N_2O_3$ is 424; ES+ MS yielded a mass of 424, as expected for the molecular ion (M+).

The fourth spiropyrrolizidine (i.e., derived from L-proline and 5-bromoisatin) was isolated as a yellow oil of 90% purity. The calculated mass for $C_{27}H_{23}N_2O_2Br$ is 486 for $^{79}Br$ and 488 for $^{81}Br$; ES+ MS yielded masses of 487 and 489, as expected for M+H+.

Figure 5A:
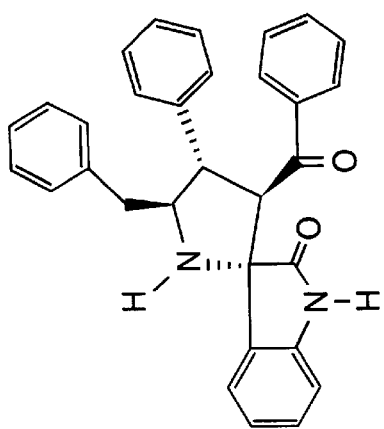
FIGS. 5a to 5c are a series of three sheets of drawings of several spiro[pyrrolidine-2,3'-oxindoles] made by the methods of the invention.
Figure 5A:
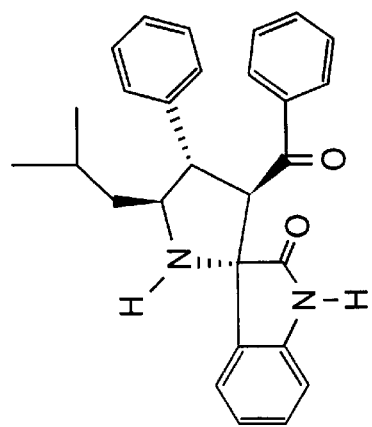
Figure 5A:
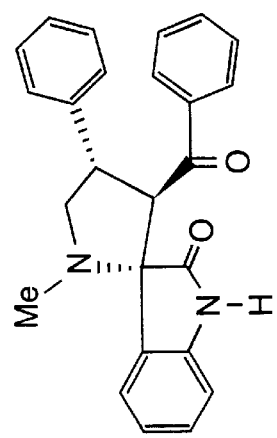
Figure 5A:
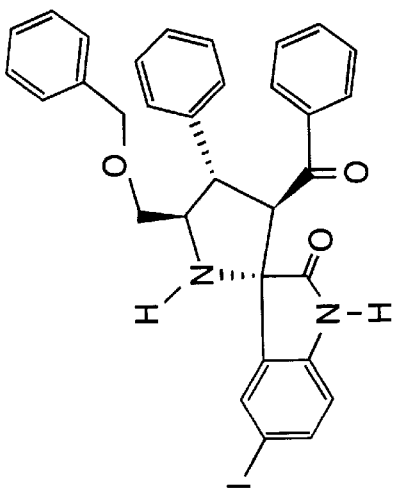
Figure 5A:
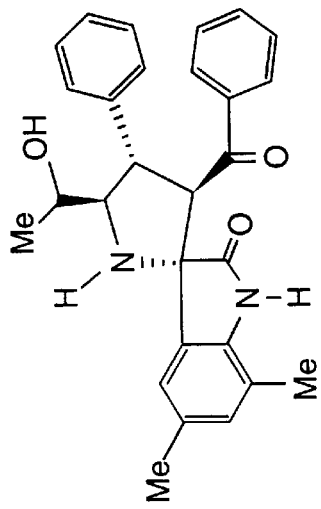
Figure 5A:
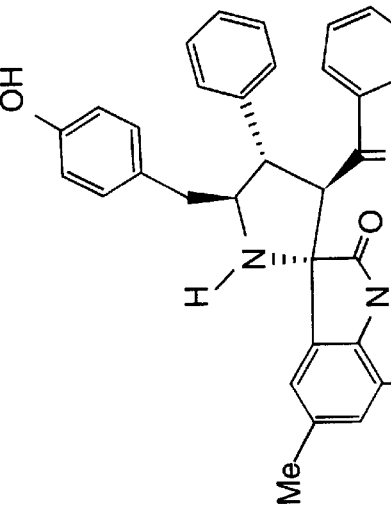
Figure 5B:
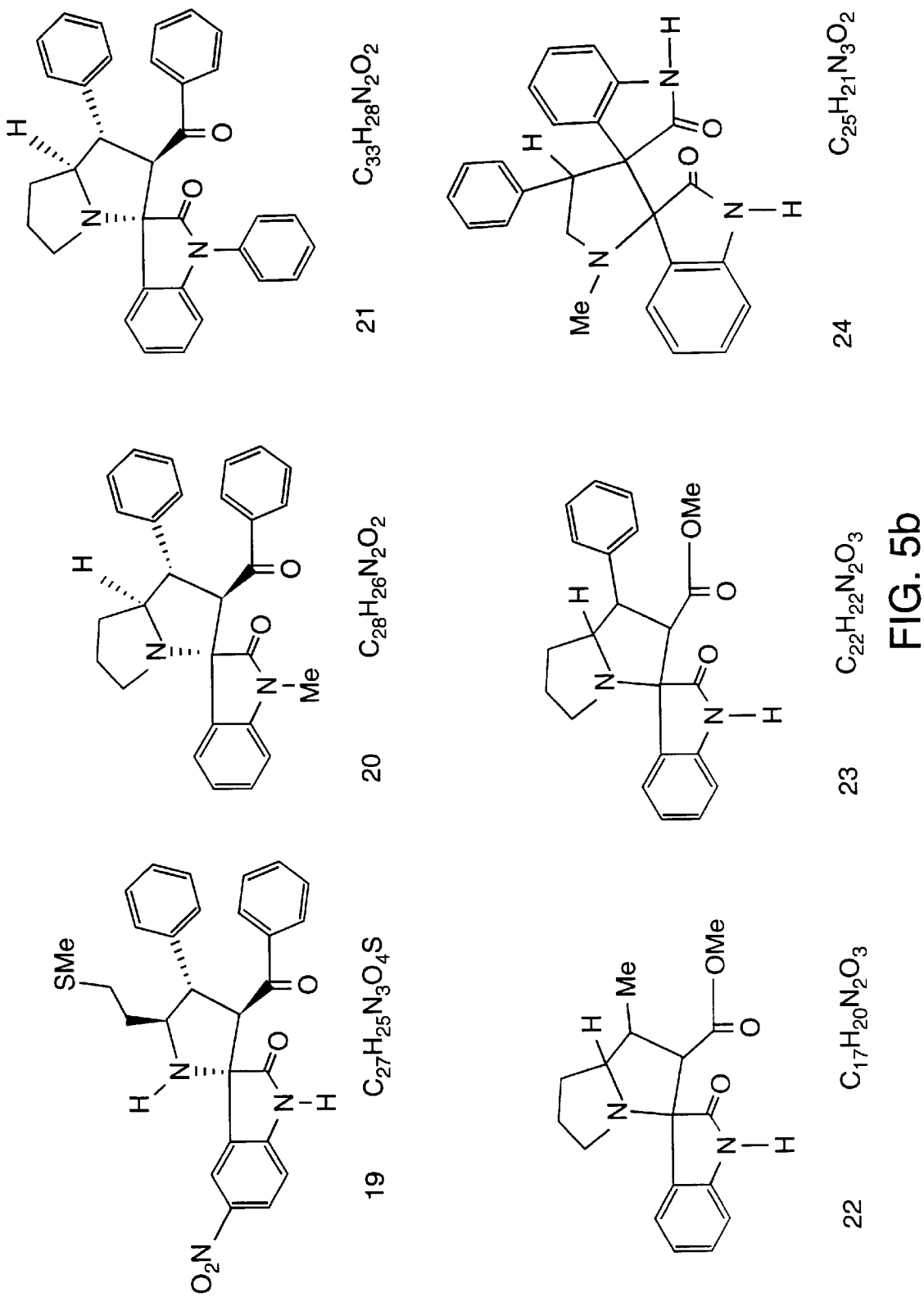
Figure 5C:
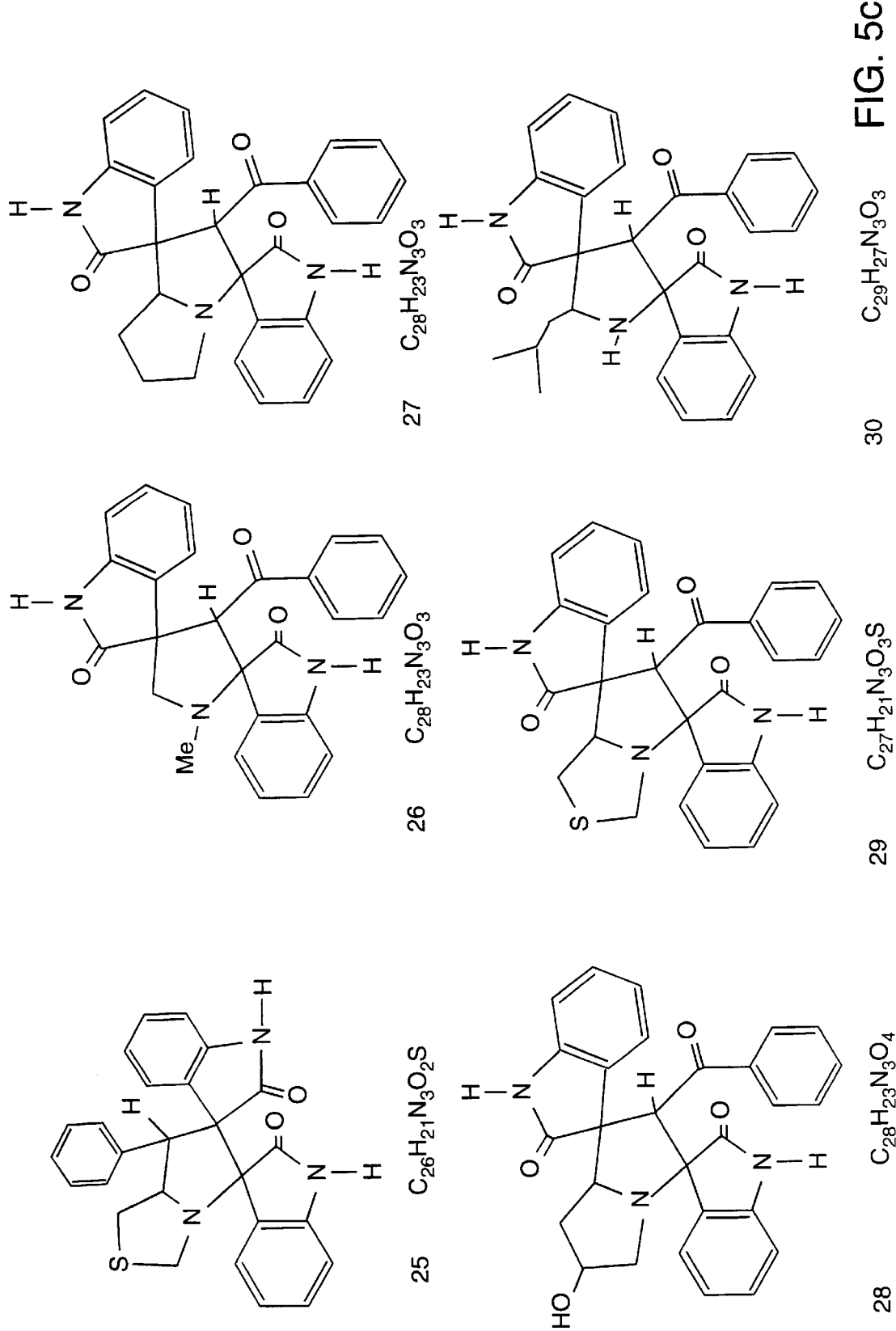

Other spiropyrrolidines were also prepared from chalcones and analyzed. Certain of these compounds are shown in FIGS. 5a to 5c. The calculated mass of the spiropyrrolidine 13 derived from sarcosine, chalcone, and isatin (i.e., $C_{25}H_{22}N_2O_2$) is 382; ES+ MS yielded a mass of 382, as expected for the molecular ion M+. The calculated mass of the spiropyrrolidine 14 derived from L-leucine, chalcone, and isatin (i.e., $C_{28}H_{28}N_2O_2$) is 424; ES+ MS yielded a mass of 424, as expected for the molecular ion M+. The calculated mass of the spiropyrrolidine 15 derived from L-phenylalanine, chalcone, and isatin (i.e., $C_{31}H_{26}N_2O_2$) is 458; ES+ MS yielded a mass of 458, as expected for the molecular ion M+. The calculated mass of the spiropyrrolidine 16 derived from L-tyrosine, chalcone, and 5,7-dimethylisatin (i.e., $C_{33}H_{30}N_2O_3$) is 502; ES+ MS yielded a mass of 503, as expected for the molecular ion M+H+. The calculated mass of the spiropyrrolidine 17 derived from L-threonine, chalcone, and 5,7-dimethylisatin (i.e., $C_{28}H_{28}N_2O_3$) is 440; ES+ MS yielded a mass of 440, as expected for the molecular ion M+. The calculated mass of the spiropyrrolidine 18 derived from O-benzyl-(D,L)-serine, chalcone, and 5-iodoisatin (i.e., $C_{32}H_{27}N_2O_3I$) is 614; ES+ MS yielded a mass of 614, as expected for the molecular ion M+. The calculated mass of the spiropyrrolidine 19 derived from L-methionine, chalcone, and 5-nitroisatin (i.e., $C_{27}H_{25}N_3O_4S$) is 487; ES+ MS yielded a mass of 487, as expected for the molecular ion M+. The calculated mass of the spiropyrrolidine 20 derived from L-proline, chalcone, and 1-methylisatin (i.e., $C_{28}H_{26}N_2O_2$) is 422; ES+ MS yielded a mass of 423, as expected for the molecular ion M+H+. The calculated mass of the spiropyrrolidine 21 derived from L-proline, chalcone, and 1-phenylisatin (i.e., $C_{33}H_{28}N_2O_2$) is 484; ES+ MS yielded a mass of 484, as expected for the molecular ion M+.

Spiropyrrolidines and spiro-spiropyrrolidines were also prepared, starting with acrylate esters and vinyl oxindoles, and analyzed. For example, a spiropyrrolidine 22 was formed by the reaction of L-proline, methylcrotonate, and isatin. The calculated mass ($C_{17}H_{20}N_2O_3$) is 300; ES+ MS yielded a mass of 301, as expected for the molecular ion M+H+. The calculated mass of the spiropyrrolidine 23 derived from L-proline, methyl cinnamate, and isatin (i.e., $C_{22}H_{22}N_2O_3$) is 362; ES+ MS yielded a mass of 362, as expected for the molecular ion M+. The calculated mass of the spiro-spiropyrrolidine 24 derived from sarcosine, arylideneoxindole 9, and isatin (i.e., $C_{25}H_{21}N_3O_2$) is 395; ES+ MS yielded a mass of 396, as expected for the molecular ion M+H+. The calculated mass of the spiro-spiropyrrolidine 25 derived from R-thiazolidinecarboxylic acid, arylideneoxindole 9, and isatin (i.e., $C_{26}H_{21}N_3O_2S$) is 439; ES+ MS yielded a mass of 439, as expected for the molecular ion M+. The calculated mass of the spiro-spiropyrrolidine 26 derived from sarcosine, vinyl oxindole 10, and isatin (i.e., $C_{28}H_{23}N_3O_3$) is 423; ES+ MS yielded a mass of 423, as expected for the molecular ion M+. The calculated mass of the spiro-spiropyrrolidine 27 derived from L-proline, vinyl oxindole 10, and isatin (i.e., $C_{28}H_{23}N_3O_4$) is 449; ES+ MS yielded a mass of 449, as expected for the molecular ion M+. The calculated mass of the spiro-spiropyrrolidine 28 derived from L-4-hydroxyproline, vinyl oxindole 10, and isatin (i.e., $C_{28}H_{23}N_3O_4$) is 465; ES+ MS yielded a mass of 465, as expected for the molecular ion M+. The calculated mass of the spiro-spiropyrrolidine 29 derived from R-thiazolidinecarboxylic acid, vinyl oxindole 10, and isatin (i.e., $C_{27}H_{21}N_3O_3S$) is 467; ES+ MS yielded a mass of 467, as expected for the molecular ion M+. The calculated mass of the spiro-spiropyrrolidine 30 derived from L-leucine, vinyl oxindole 10, and isatin (i.e., $C_{29}H_{27}N_3O_3$) is 446; ES+ MS yielded a mass of 465, as expected for the molecular ion M+.

Example 2
Screening Libraries for Thrombin Inhibitors

Human α-thrombin is purified from human plasma by isolation of prothrombin followed by treatment with *Oxyuranus acutellatus* venom and purification on a sepharose column. The substrate Pefachrome™ TH is obtained from Pentapharm.

Each of the compounds from the new libraries is dissolved in dimethylsulfoxide and diluted with water to a concentration of 1 mM. Further dilutions are made into an assay buffer containing 100 mM sodium phosphate buffer, pH 7.4, 100 mM sodium chloride, and 0.1% bovine serum albumin.

Kinetic assays are carried out at 25° C. in a 96 well plate. To each well are added 50 μl of substrate (final concentration of 100 μM) and 100 μl of diluted library compound in assay buffer. The assay is initiated by adding 100 μl of α-thrombin (final concentration of 160 pM) in the assay buffer. The release of p-nitroaniline by hydrolysis of the Pefachrome substrate is followed over the course of one hour by measuring the increase in optical density at 405 nm with a microwell kinetic reader. For the wells in which inhibited steady-state rates are achieved rapidly, the inhibition constant ($K_i$) is determined by fitting the data by weighted linear regression to the Dixon equation. For slow, tight-binding inhibitors, the mechanism of inhibition is characterized by the Michaelis-Menten equation.

A 50% decrease in hydrolysis of the Pefachrome substrate in wells containing members of the library (relative to a control sample) indicates that those wells contain an inhibitor of thrombin.

Example 3
Screening Libraries for Bioseparation Ligands

The compounds from the new libraries are pooled and assayed in a competition ELISA format over the concentration range of 0.1 nM to 500 μM. Microtiter plates are coated overnight at 4° C. with recombinant gp120 antigen (env 2–3; 0.2 μg per well with 50 mM borate, pH 9.0). A 50 μl aliquot of the compound pool is incubated with 50 μl of diluted IgG (26 μM stock solution diluted 1:50,000) in 0.5 M sodium chloride, 1% Triton X-100, 0.1% casein, and 250 mM phosphate buffer, pH 7.5, for 1 hour at 37° C. The plates are washed six times with a wash buffer (150 mM sodium chloride and 0.5% Triton X-100) and incubated with 100 μl of horseradish peroxidase-conjugated goat anti-mouse antibody (1 mg/ml stock solution diluted 1:1,000) for 1 hour at 37° C. The plates are washed again as above and the bound, conjugated antibody is quantified by color development with 100 μl of o-phenylenediamine at 5 mg/ml in 50 mM sodium citrate and 0.02% hydrogen peroxide at pH 5.1. The plates are read in a microplate reader at 450 nm.

The most inhibitory compounds are then identified. Anti-gp120 monoclonal antibody (100 nmol, IgG, Chiron 26-8-F8-E3) is incubated with each inhibitory compound for 1 hour at 25° C. Each of the compounds is supplied in a 10-fold molar excess (relative to antibody) in 200 mM sodium chloride and 10 mM phosphate buffer, pH 7.5. The mixture is then fractionated by gel filtration on a sephadex fast desalting column in 150 mM sodium chloride and 10 mM phosphate buffer, pH 7.5. The first eluted peak is the antibody-compound complex. The compounds are then dissociated from the antibody using 1% aqueous trifluoroacetic acid and analyzed by reverse phase HPLC. The compounds are then identified by mass spectroscopy, nuclear magnetic resonance, and infrared spectrometry. These inhibitory compounds are concluded to exhibit strong binding. Affinity columns are prepared by immobilizing the compounds on a solid support.

Example 4
Screening Libraries for Metalloproteinase Activity

Matrix metalloproteinase (MMPase) activity is measured in synovial cell culture supernatants using an assay based on the cleavage of a synthetic, fluorogenic substrate, 7-methoxycoumarin-4-yl)acetyl-L-prolyl-L-leucyl-L-glycyl-L-leucyl-(3-[2,4-dinitrophenyl]-L-2,3-diaminopropionyl)-L-alanyl-L-arginine. The supernatants and a medium-only control are incubated with the substrate at a final concentration of 6 μM for 2 hours at 37° C. To determine the level of MMP-specific peptide cleavage, two series of reactions are carried out: a first containing a broad spectrum MMPase inhibitor, BB-2116, at a final concentration of 10 μM, and a second containing each of the compounds of the new libraries. The reactions are stopped by addition of an equal volume of 3% aqueous acetic acid to the reaction mixtures. The fluorescence intensity for each sample is measured in a fluorimeter at excitation and emission wavelengths of 320 and 405 nm, respectively. MMPase activity is determined by subtraction of the fluorescence intensity of the culture medium blank and BB-2116 control values from the library compound-containing sample values. Those compounds that reduce MMPase activity by more than 50% are concluded to be MMPase inhibitors.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, many modifications can be made to adapt a particular reaction, material, library, process step or steps, to the objectives, spirit, and scope of the present invention. For example, dipolarophiles other than chalcones, acrylate esters, vinyl oxindoles, fumarates, maleates, maleimides, cinnamonitriles, nitroolefins, acrylonitriles, vinyl sulfones, or vinyl sulfoxides can be used to generate libraries drawn from other classes of complex heterocyclic ring systems. Furthermore, the compounds of the new libraries can be used as building blocks for other libraries. For example, the spiro[pyrrolidine-2,3'-oxindoles] can be reacted with each other to form dimers, trimers, or higher oligomers (e.g., using a linker molecule). The new methods are also compatible with computational methods (e.g., virtual screening), wherein computerized molecular modelling studies are used to predict which libraries compounds are the most likely to yield the most lead compounds.

What is claimed is:

1. A spiro compound represented by the formula:

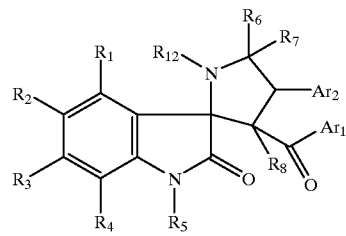

where $R_1$ to $R_4$ are independently selected from the group consisting of hydrogen, alkyl, aryl, carbocyclic, fluoro, chloro, bromo, iodo, thio, hydroxyl, alkylthio, alkoxy, carboxy, sulfonyl, nitro, cyano, amido, keto, formyl, and amino groups; $R_5$ to $R_8$ and $R_{12}$ are independently selected from the group consisting of hydrogen, alkyl, aryl, and carbocyclic groups; and $Ar_1$ and $Ar_2$ are independently selected from the group consisting of substituted and unsubstituted aryl and heteroaryl groups.

2. The compound of claim 1, wherein $Ar_1$ and $Ar_2$ are both phenyl.

3. The compound of claim 1, wherein at least one of $R_6$ and $R_7$ is hydrogen.

4. The compound of claim 1, wherein $R_6$ or $R_7$, together with the carbon to which it is attached, and $R_{12}$, together with the nitrogen to which it is attached, form a ring.

5. The compound of claim 1, wherein one of $Ar_1$ and $Ar_2$ is a heteroaryl group.

6. A method for preparing a spiro[pyrrolidine-2,3'-oxindole] compound of claim 1, the method comprising:

reacting an isatin with an α-amino acid to form an azomethine ylide; and reacting the azomethine ylide with a chalcone to form the spiro[pyrrolidine-2,3'-oxindole] compound of claim 1.

7. The method of claim 6, wherein the α-amino acid is a naturally occurring amino acid.

8. The method of claim 6, wherein the α-amino acid is a cyclic amino acid.

9. The method of claim 6, wherein the azomethine ylide is reacted with a chalcone in a solvent.

10. The method of claim 9, wherein the solvent comprises dioxane.

11. The method of claim 6, wherein both reacting steps are conducted in the same solvent.

12. The method of claim 11, wherein the method is conducted with a single reaction vessel.

13. The method of claim 6, wherein one or more steps of the method is conducted at a temperature of 60 to 95° C.

14. The method of claim 6, wherein one or more steps of the method is conducted at a temperature of 80 to 85° C.

15. The method of claim 6, wherein the isatin has the structural formula:

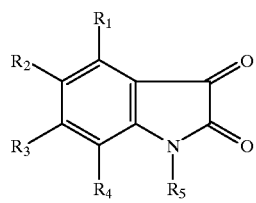

wherein $R_1$ to $R_4$, independently, is a hydrogen, alkyl, aryl, carbocyclic, fluoro, chloro, bromo, iodo, thio, hydroxyl, alkylthio, alkoxy, carboxy, sulfonyl, nitro, cyano, amido, keto, formyl, or amino group, and wherein $R_5$ is hydrogen, or an alkyl, aryl, or carbocyclic group.

16. The method of claim 15, wherein $R_5$ is hydrogen.

17. The method of claim 15, wherein $R_5$ is an aryl group.

18. The method of claim 15, wherein $R_5$ is an alkyl group.

19. The method of claim 6, wherein the isatin is selected from the group consisting of 5-fluorisatin, 1-methylisatin, 5-nitroisatin, 5-iodoisatin, 1- phenylisatin, 5-chloro-7-methylisatin, 5,7-dimethylisatin, 5-bromoisatin, 5-chloroisatin, 5- trifluoromethoxyisatin, 1-benzylisatin, 1-(3-chlorobenzyl) isatin, 1-(4-methoxybenzyl)isatin, and 1-allylisatin.

20. The method of claim 6, wherein the α-amino acid is selected from the group consisting of sarcosine, L-valine, L-methionine, L-methionine sulfoxide, L-methionine sulfone, L-alanine, L-glutamine, L-threonine, D-serine, L-phenylalanine, glycine, L-leucine, O-benzyl- (D,L)-serine, O-methyl-L-tyrosine, L-isoleucine, L-proline, 4-hydroxy-L-proline, R-thiazolidine carboxyl acid, L-tryptophan, and L-phenylglycine.

21. The method of claim 6, further comprising adding an amount of a base sufficient to dissolve the α-amino acid.

22. The compound of claim 1, wherein $R_5$ is hydrogen.

23. The compound of claim 1, wherein $R_5$ is an alkyl group.

24. The compound of claim 1, wherein $R_5$ is an aryl group.

* * * * *

UNITED STATES PATENT AND TRADEMARK OFFICE
CERTIFICATE OF CORRECTION

PATENT NO. : 6,114,540
DATED : September 5, 2000
INVENTOR(S) : Demosthenes Fokas; David L. Coffen; William J. Ryan It is certified that error appears in the above-identified patent and that said Letters Patent is hereby corrected as shown below:

Column 2,
Lines 8-9, delete "spiro[pyrrolidine-2,3,'-oxindole]" and substitute -- spiro[pyrrolidine-2,3'-oxindole] --;

Column 5,
Lines 33-34, delete "-OC(O)$R_a$-N-$R_b R_d$" and substitute -- OC(O)$R_a$-N$R_b R_d$ --;

Column 7,
Lines 46-55, the formula should appear as follows:

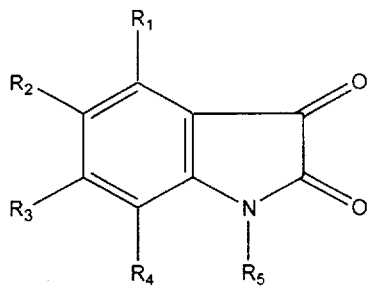

Column 10,
Line 33, delete "850°" and substitute -- 85° --;
Line 48, delete "staring" and substitute -- starting --;

Column 17,
Line 63, delete "M+" and substitute -- $M^+$ --.

Column 20, claim 12,
Line 61, delete "with" and substitute -- within --;

Column 21, claim 19,
Line 21, delete "5-fluorisatin" and substitute -- 5-fluoroisatin --;

UNITED STATES PATENT AND TRADEMARK OFFICE
CERTIFICATE OF CORRECTION

PATENT NO.    : 6,114,540
DATED         : September 5, 2000
INVENTOR(S)   : Demosthenes Fokas; David L. Coffen; William J. Ryan It is certified that error appears in the above-identified patent and that said Letters Patent is hereby corrected as shown below:

<u>Column 21, claim 19,</u>
Lines 21-22, between "1-methylisatin," and "5-nitroisatin,", insert -- 5-methylisatin --.

Signed and Sealed this

Twelfth Day of February, 2002

Attest:

JAMES E. ROGAN
*Attesting Officer*   *Director of the United States Patent and Trademark Office*